US011391680B2

(12) United States Patent
Saito

(10) Patent No.: US 11,391,680 B2
(45) Date of Patent: Jul. 19, 2022

(54) X-RAY FLUORESCENCE ANALYZER AND X-RAY FLUORESCENCE ANALYSIS METHOD

(71) Applicant: Shimadzu Corporation, Kyoto (JP)

(72) Inventor: Yuta Saito, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 17/048,881

(22) PCT Filed: Jun. 8, 2018

(86) PCT No.: PCT/JP2018/022117
§ 371 (c)(1),
(2) Date: Oct. 19, 2020

(87) PCT Pub. No.: WO2019/234935
PCT Pub. Date: Dec. 12, 2019

(65) Prior Publication Data
US 2021/0161493 A1 Jun. 3, 2021

(51) Int. Cl.
*G01N 23/223* (2006.01)
(52) U.S. Cl.
CPC ..... *G01N 23/223* (2013.01); *G01N 2223/306* (2013.01); *G01N 2223/309* (2013.01); *G01N 2223/314* (2013.01); *G01N 2223/316* (2013.01)
(58) Field of Classification Search
CPC .......... G01N 23/223; G01N 2223/309; G01N 2223/314; G01N 2223/316
See application file for complete search history.

(56) References Cited

U.S. PATENT DOCUMENTS

2008/0212739 A1* 9/2008 Fukai .................. G01N 23/223
378/86
2015/0023466 A1 1/2015 Melman
2015/0313558 A1* 11/2015 Melman ................ A61B 6/545
378/62

FOREIGN PATENT DOCUMENTS

JP        06-324009 A      11/1994
JP        06324009 A    *  11/1994
JP        2002340825 A  *  11/2002
JP        2003-229084 A    8/2003
JP        2003229084 A  *   8/2003
(Continued)

OTHER PUBLICATIONS

Notice of Reasons for Refusal for corresponding Japanese Patent Application JP 2020-523970 dated Aug. 30, 2021.
(Continued)

*Primary Examiner* — Chih-Cheng Kao
(74) *Attorney, Agent, or Firm* — Muir Patent Law, PLLC

(57) ABSTRACT

A support unit and a collimator are relatively rotated about the axis of rotation by a rotation driving device. The collimator has a blocking region that blocks X-rays and a transmission region that allows X-rays to pass therethrough. The transmission region has a vertex positioned on the axis of rotation, and the circumferential length of the transmission region increases proportionally as it advances outward from the vertex. A sample supported by the support unit is irradiated with X-rays by an X-ray source through the transmission region of the collimator, and the fluorescent X-rays from the sample are detected by the detector. The analysis of a composition of a sample is performed based on the fluorescent X-rays detected by the detector.

12 Claims, 7 Drawing Sheets

(56) References Cited

FOREIGN PATENT DOCUMENTS

| JP | 2006-317370 A | 11/2006 | | |
|----|---------------|---------|---|---|
| JP | 2011-200532 A | 10/2011 | | |
| JP | 2011200532 A | * 10/2011 | ............. | A61B 6/484 |
| JP | 2015-513423 A | 5/2015 | | |
| JP | 2016-501656 A | 1/2016 | | |

OTHER PUBLICATIONS

International Search Report for International Patent Application No. PCT/JP2018/022117 dated Aug. 14, 2018.
Written Opinion of the International Searching Authority with respect to International Patent Application No. PCT/JP2018/022117, dated Aug. 14, 2018, submitted with a machine translation.

* cited by examiner

X-RAY FLUORESCENCE ANALYZER AND X-RAY FLUORESCENCE ANALYSIS METHOD

TECHNICAL FIELD

The present invention relates to an X-ray fluorescence analyzer and an X-ray fluorescence analysis method for analyzing a sample by fluorescent X-rays.

BACKGROUND ART

In an X-ray fluorescence analyzer, a sample is irradiated with X-rays from an X-ray source to excite the sample, so that fluorescent X-rays are released from the sample. The number of photons per hour (hereinafter simply referred to as the "number of photons") of the fluorescent X-rays released from the sample is detected by a detector. The detector outputs a detection signal indicating the detected number of photons. Based on the detection signal outputted by the detector, the elements contained in the sample are analyzed.

There is a limit on the number of photons that can be detected without saturating the detection signal. Therefore, even when the intensity (dose) of X-rays emitted by an X-ray source is minimized, the detection signal may sometimes be saturated. To prevent this, a member called "collimator" is arranged between the X-ray source and the sample. The collimator is a plate-like member having an opening and attenuates the X-rays emitted to a sample by blocking a part of the X-rays emitted from the X-ray source.

On the other hand, Patent Document 1 describes an X-ray reduction system for use in the field of medicine rather than in the field of analysis techniques using fluorescent X-rays. In this X-ray reduction system, an X-ray source is arranged below a bed that allows X-rays to pass therethrough, a collimator is placed above the bed, and an image intensifier is arranged above the collimator. The collimator has a disc shape and is formed with a circular aperture in the center of the collimator. A patient lies on the bed and an operator is beside the patient.

A patient is irradiated with X-rays from the X-ray source in response to an operation by an operator. A part of the X-rays emitted to the patient passes through the circular aperture formed in the collimator to reach the image intensifier. Based on the X-rays arrived at the image intensifier, an image with high image quality in the region of interest is generated. Further, the other part of the X-rays is blocked by the portion of the collimator except for the circular aperture, thereby reducing the exposure to the operator near the patient. Patent Document 1: Japanese Translation of PCT International Application Publication No. 2016-501656

SUMMARY OF THE INVENTION

Problems to be Solved by the Invention

On the other hand, in the field of analytical techniques using fluorescent X-rays, when the intensity of X-rays emitted to a sample is spatially non-uniform, the composition of the entire sample cannot be correctly analyzed. In particular, this issue becomes more apparent when analyzing a sample containing non-uniformly distributed elements. Therefore, it is required to spatially and uniformly attenuate X-rays to be emitted to a sample.

It is an object of the present invention to provide an X-ray fluorescence analyzer and an X-ray fluorescence analysis method capable of spatially and uniformly attenuating X-rays to be emitted to a sample.

Means for Solving the Problem (1) An X-ray fluorescence analyzer according to one aspect of the present invention includes:
  a support unit configured to support a sample to be analyzed;
  a collimator having a blocking region that blocks X-rays and a transmission region that allows X-rays to pass therethrough;
  an X-ray source configured to emit X-rays to the sample supported by the support unit through the transmission region of the collimator;
  a rotation driving device configured to relatively rotate the support unit and the collimator about an axis of rotation; and
  a detector configured to detect fluorescent X-rays from the sample supported by the support unit; and
  an analysis execution unit configured to analyze a composition of the sample based on the fluorescent X-rays detected by the detector,
  wherein the transmission region has a vertex positioned on the axis of rotation, and
  wherein a circumferential length of the transmission region increases proportionally as it advances outward from the vertex.

In this X-ray fluorescence analyzer, the support unit and the collimator are relatively rotated about the axis of rotation by the rotation driving device. The sample supported by the support unit is irradiated with X-rays from the X-ray source through the transmission region of the collimator, and the fluorescent X-rays from the sample are detected by the detector. The analysis of the composition of the sample is performed based on the fluorescent X-rays detected by the detector.

According to this configuration, a part of the X-rays emitted by the X-ray source is blocked by the blocking region of the collimator, and the other part of the X-rays passes through the transmission region of the collimator. Here, the transmission region has a vertex positioned on the axis of rotation, and the circumferential length of the transmission region increases proportionally as it advances outward from the vertex. Therefore, the X-rays pass through the transmission region of the collimator while the support unit and the collimator are relatively rotated by one revolution, so that the X-rays emitted to each part of the sample become spatially uniform. This makes it possible to spatially and uniformly attenuate the X-rays to be emitted to the sample.

(2) The transmission region may have a sector shape. In this case, the collimator in which the circumferential length of the transmission region proportionally increases as it advances outward from the vertex can be realized by a simple shape.

(3) The transmission region may be an opening. In this case, the X-rays to be emitted to each portion of the sample by passing through the transmission region of the collimator can be made spatially uniform more easily.

(4) It may be configured such that the collimator is fixed and the support unit is rotatable relative to the collimator. In this case, it is possible to relatively rotate the support unit and the collimator about the axis of rotation with a simple configuration.

(5) The collimator may be configured to be variable in a circumferential length of the transmission region. In this case, depending on the composition of the sample, the circumferential length of the transmission region of the collimator can easily be changed. With this, it is possible to uniformly attenuate X-rays to appropriate intensity according to the composition of the sample.

(6) It may be configured such that the X-ray fluorescence analyzer further includes an intensity control unit configured to control intensity of the X-rays emitted by the X-ray source. In this case, the intensity of X-rays can be appropriately adjusted according to the composition of the sample.

(7) It may be configured such that the X-ray fluorescence analyzer further includes a determination unit configured to determine whether or not a detection signal indicating a detection amount of the fluorescent X-rays detected by the detector is saturated, and the intensity control unit controls the X-ray source so that the intensity of X-rays to be emitted increases to an extent that the detection signal is not saturated based on a determination result by the determination unit. In this case, it is possible to perform an analysis of the sample with high efficiency regardless of the composition of the sample.

(8) An X-ray fluorescence analysis method according to another aspect of the present invention includes the steps of:
relatively rotating a support unit for supporting a sample to be analyzed and a collimator having a blocking region that blocks X-rays and a transmission region that allows X-rays to pass therethrough around an axis of rotation by a rotation driving device;
emitting X-rays by an X-ray source to the sample supported by the support unit through the transmission region of the collimator;
detecting fluorescent X-rays from the sample supported by the support unit by the detector; and
analyzing a composition of the sample based on the fluorescent X-rays detected by the detector,
wherein the transmission region has a vertex positioned on an axis of rotation, and
wherein a circumferential length of the transmission region increases proportionally as it advances outward from the vertex.

According to the X-ray fluorescence analysis method, the X-rays passing through the transmission region of the collimator while the support unit and the collimator are relatively rotated by one revolution become spatially uniform to be emitted to each part of the sample. This makes it possible to spatially and uniformly attenuate the X-rays to be emitted to the sample.

(9) It may be configured such that the step of rotating includes rotating the support unit relative to the collimator that is fixed. In this case, it is possible to relatively rotate the support unit and the collimator about the axis of rotation with a simple configuration.

Effects of the Invention

According to the present invention, X-rays can be spatially and uniformly attenuated.

BRIEF DESCRIPTION OF THE DRAWINGS

EMBODIMENTS FOR CARRYING OUT THE INVENTION (1) Configuration of X-Ray Fluorescence Analyzer Hereinafter, an X-ray fluorescence analyzer and an X-ray fluorescence analysis method according to an embodiment of the present invention will be described in detail with reference to the attached drawings. FIG. 1 is a diagram showing a configuration of the X-ray fluorescence analyzer according to an embodiment of the present invention. FIG. 2 is a plan view showing a configuration of a collimator 40 of FIG. 1. As shown in FIG. 1, the X-ray fluorescence analyzer 100 is a wavelength dispersive type X-ray fluorescence analyzer and includes a rotation driving device 10, a support unit 20, an X-ray source 30, a collimator 40, an analyzing crystal 50, a detector 60, and a processing device 70. Note that the X-ray fluorescence analyzer 100 may be an energy-dispersive type X-ray fluorescence analyzer.

Figure 1:
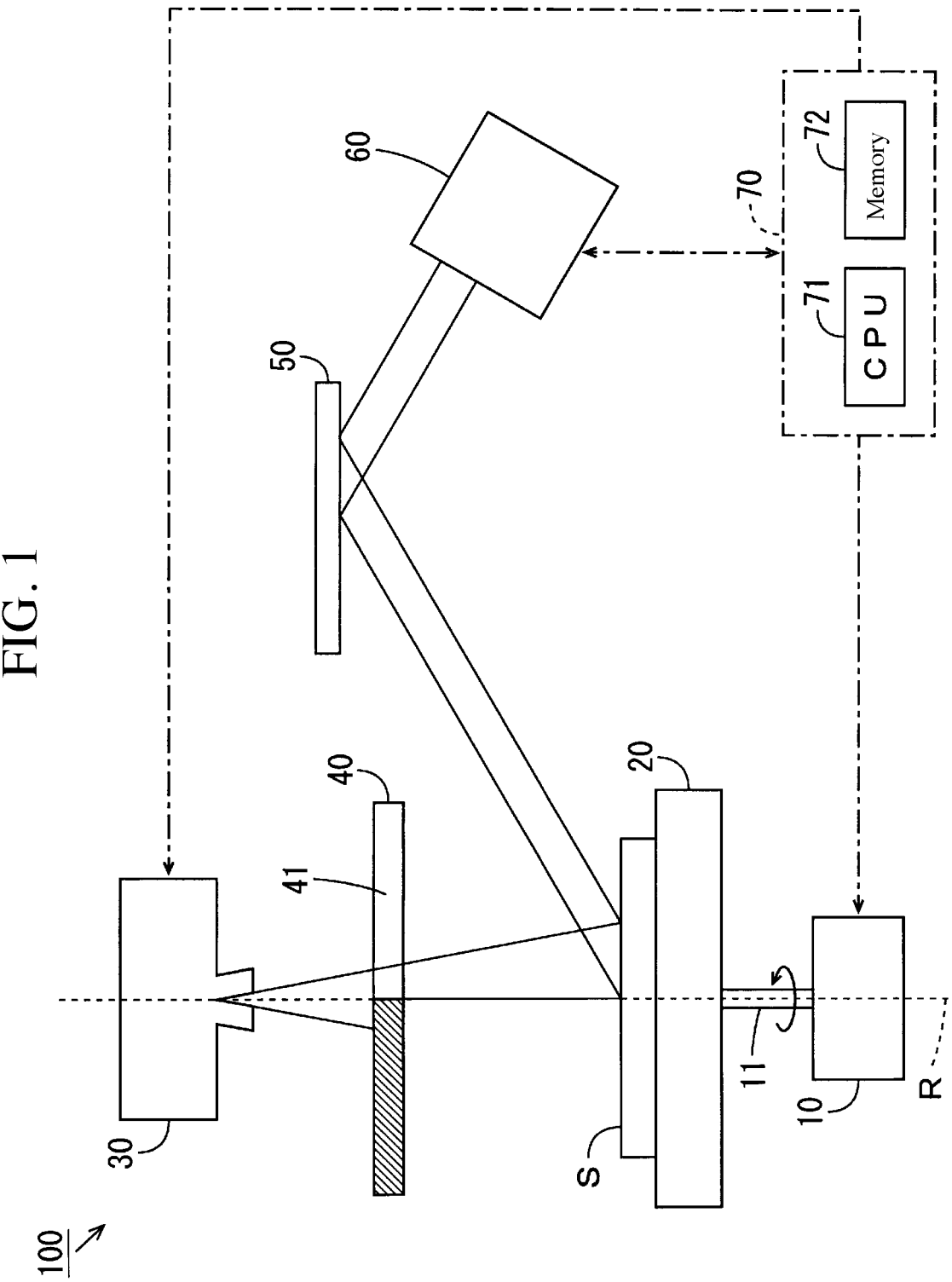
FIG. 1 is a diagram showing a configuration of an X-ray fluorescence analyzer according to an embodiment of the present invention.

The rotation driving device 10 is, for example, an electric motor and has an upwardly extending drive shaft 11. The support unit 20 is a sample platform of a disc shape and is attached to the upper end of the drive shaft 11 of the rotation driving device 10. The support unit 20 supports a sample S to be analyzed. The support unit 20 is rotated at a constant rate by the rotation driving device 10 about the axis of rotation R parallel to the vertical direction. The X-ray source 30 is arranged above the support unit 20 and emits X-rays to the sample S supported by the support unit 20.

The collimator 40 is a plate-like member made of a material (e.g., lead) that blocks X-rays and is arranged between the support unit 20 and the X-ray source 30. The collimator 40 has a disc shape and is arranged so that the center of the disc overlaps with the axis of rotation R of the rotation driving device 10.

Figure 2:
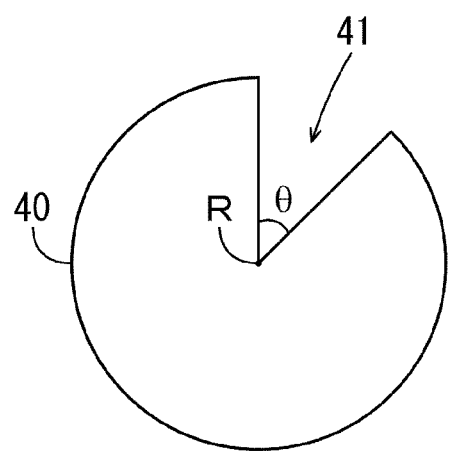
FIG. 2 is a plan view showing a configuration of a collimator of FIG. 1.

As shown in FIG. 2, the collimator 40 is formed with a sector-shaped opening 41. The vertex of the sector shape of the opening 41 overlaps with the axis of rotation R. Note that the vertex of the sector shape means the intersection of the two linear edges of the sector shape extending along the radial direction thereof. The central angle of the sector shape is θ. The value of the central angle θ is not specifically limited. In the example of FIG. 2, the opening 41 is a cut-out portion and the outer peripheral portion (arc) of the sector shape is exposed laterally from the side surface of the collimator 40. The portion of the collimator 40 except for the opening 41 is a blocking region that blocks X-rays.

As shown in FIG. 1, the collimator 40 blocks a part of the X-rays emitted from the X-ray source 30 and allows the other part of the X-rays to pass therethrough. Since the support unit 20 is rotated at a constant rate, the X-rays that have passed through the collimator 40 are uniformly emitted to the respective portions of the sample S in a time-division manner. When averaged with time, the X-rays emitted to the respective portions of the sample S are spatially and uniformly attenuated.

In this embodiment, the support unit 20 is rotated while the collimator 40 is not rotated, but the present invention is not limited thereto. It is sufficient that the support unit 20 and the collimator 40 are relatively rotated. Therefore, in cases where the collimator 40 is rotatably held, it may be configured such that the collimator 40 is rotated while the support unit 20 is not rotated.

When the sample S is irradiated with X-rays, the sample S is excited to release fluorescent X-rays. The analyzing crystal 50 is, for example, a reflection grating, and spectrally disperses the fluorescent X-rays emitted from the sample S so as to reflect the fluorescent X-rays at different angles for each wavelength. The analyzing crystal 50 may be a transmission-type diffraction grating.

The detector 60 is, for example, a proportional counter tube, detects the number of photons (hereinafter, simply referred to as the number of photons) of the fluorescence X-rays per unit time for each wavelength spectrally dispersed by the analyzing crystal 50, and outputs a detection signal indicating the detected number of photons. In cases where the X-ray fluorescence analyzer 100 is an energy-dispersive X-ray fluorescence analyzer, the detector 60 may be a solid-state detector.

The processing device 70 includes a CPU (Central Processing Unit) 71 and a memory 72. The memory 72 is composed of a RAM (Random Access Memory), a ROM (Read Only Memory), a hard disk or a solid-state memory, or the like, and stores an analysis program. The processing device 70 controls the operations of the rotation driving device 10, the X-ray source 30, and the detector 60, and performs a quantitative analysis or a qualitative analysis of the elements contained in the sample S based on the detection signal outputted by the detector 60. The details of the processing device 70 will be described later.

(2) Analysis Processing

Figure 3:
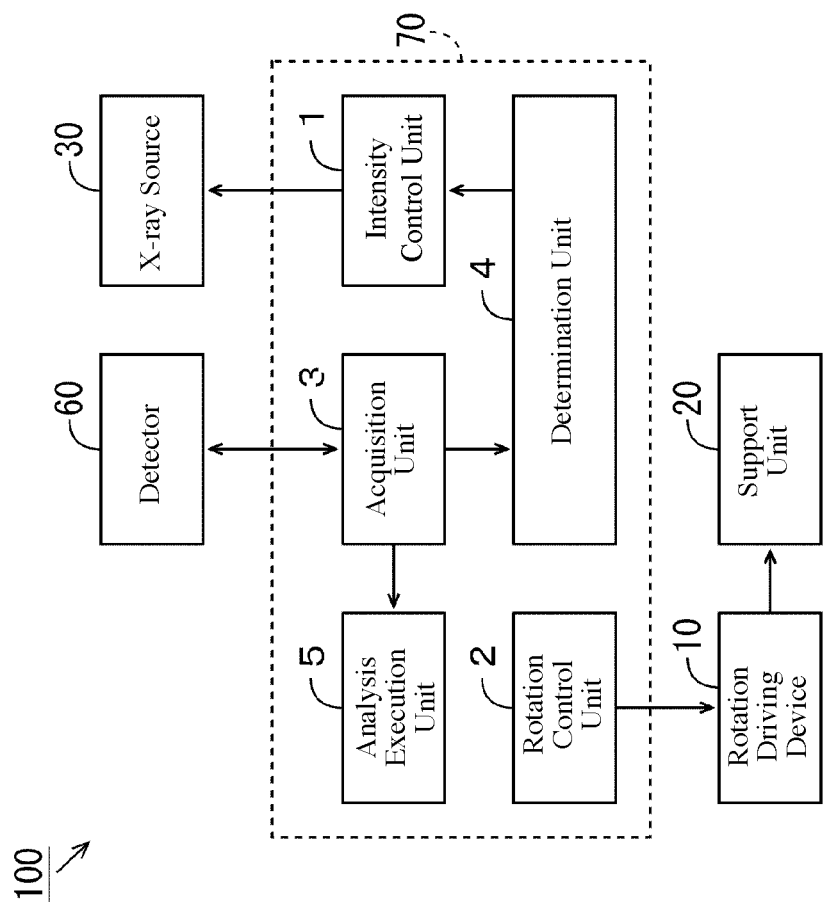
FIG. 3 is a diagram showing a configuration of a functional portion of a processing device of FIG. 1.
Figure 4:
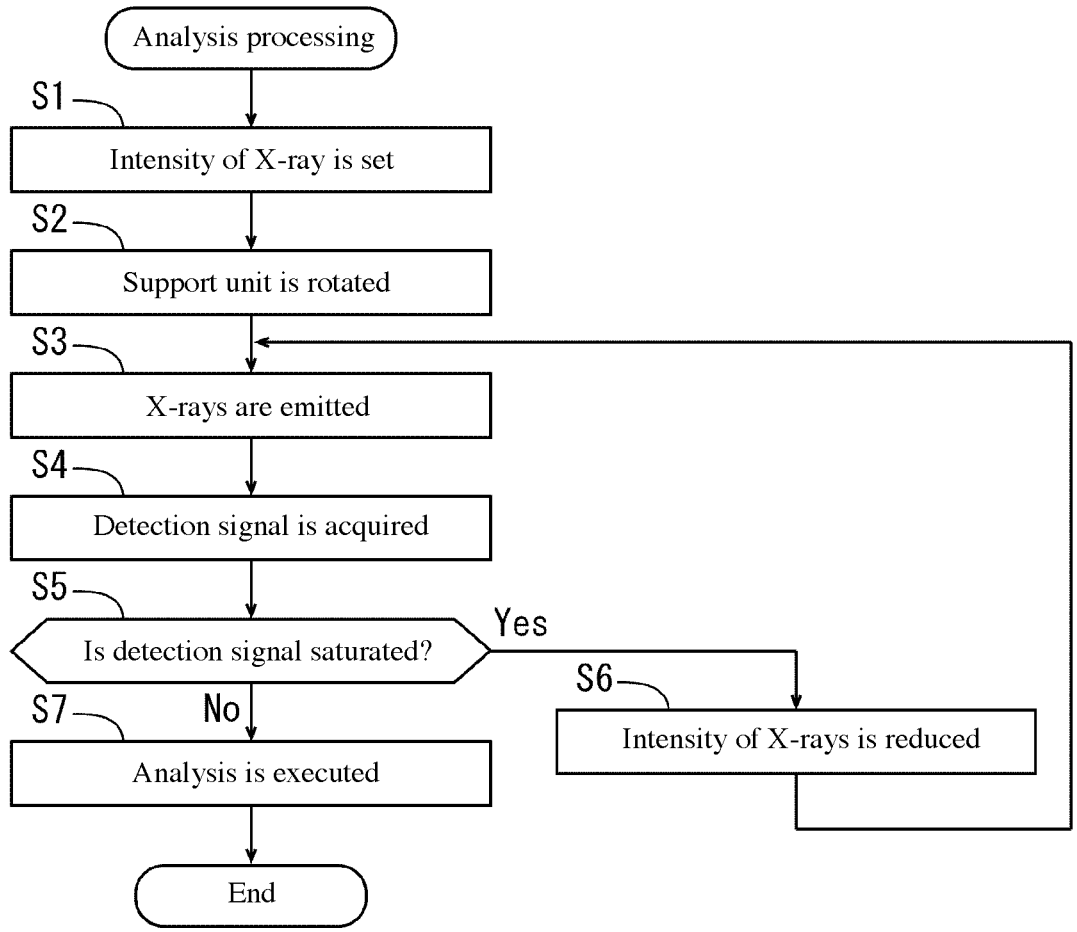
FIG. 4 is a flowchart showing an algorithm of analysis processing performed by an analysis program.

FIG. 3 is a diagram showing a configuration of a functional portion of the processing device 70 of FIG. 1. FIG. 4 is a flowchart showing the algorithm of the analysis processing performed by an analysis program. As shown in FIG. 3, the processing device 70 includes, as functional portions, an intensity control unit 1, a rotation control unit 2, an acquisition unit 3, a determination unit 4, and an analysis execution unit 5. The functional portions of the processing device 70 are realized by executing an analysis program stored in the memory 72 by the CPU 71 of FIG. 1. A part or all of the functional portions of the processing device 70 may be implemented by hardware, such as, e.g., electronic circuits.

A user sets a sample S to be analyzed in an autosampler (not shown) and instructs the X-ray fluorescence analyzer 100 to start the analysis. With this, the sample S is supported by the support unit 20 and the analysis processing is started. Hereinafter, the analysis processing will be described with reference to the processing device 70 of FIG. 3 and the flowchart of FIG. 4.

First, the intensity control unit 1 sets the intensity (dose) of X-rays emitted from the X-ray source 30 (Step S1). The rotation control unit 2 controls the rotation driving device 10 to rotate the support unit 20 (Step S2). The rotational rate of the support unit 20 is, for example, 720 degrees/sec. Step S2 is executed after Step S1, but the present invention is not limited thereto. Step S2 may be executed prior to Step S1, or may be executed concurrently with Step S1.

Next, the intensity control unit 1 controls the X-ray source 30 to emit X-rays having the intensities set in Step S1 (Step S3). With this, X-rays are emitted to the sample S on the rotating support unit 20 from the X-ray source 30 through the collimator 40, and the fluorescent X-rays are released from the sample S. The acquisition unit 3 detects the number of photons of the X-ray fluorescence released from the sample S by controlling the detector 60, and acquires the detection signal outputted by the detector 60 (Step S4).

The determination unit 4 determines whether or not the detection signal acquired in Step S4 is saturated (Step S5). When the detection signal is saturated, the intensity control unit 1 reduces the intensity of the X-rays emitted by the X-ray source 30 set in Step S1 (Step S6), and returns to Step S2. Steps S3 to S6 are repeated until the detection signal becomes no longer saturated.

When the detection signal is not saturated in Step S5, the analysis execution unit 5 executes the analysis of the composition of the sample S based on the detection signal acquired in Step S4 (Step S7). Specifically, the analysis execution unit 5 generates a spectrum indicating the relationship between the wavelength of the fluorescent X-rays and the number of photons of fluorescent X-rays and identifies the composition of the sample S from the generated spectrum. At this time, the analysis execution unit 5 can correct the intensity of the X-rays emitted to the sample S based on the ratio of the area of the opening 41 to the entire area of the collimator 40. After Step S7, the analysis execution unit 5 ends the analysis processing.

In Step S1, in cases where the intensity of the X-rays emitted by the X-ray source 30 is set low enough so that the detection signal outputted by the detector 60 is not saturated, Steps S5 and S6 may be skipped in the analysis processing. In this case, the processing device 70 does not include the determination unit 4.

On the other hand, in Step S1, the intensity of the X-rays emitted by the X-ray source 30 may be set to be sufficiently high so that the detection signal outputted by the detector 60 is saturated. In this case, the intensity of the X-rays is set to be large within the rage in which the detection signal is not saturated in Step S6 by repeating Steps S3 to S6. This makes it possible to execute the analysis of the sample S with high efficiency in Step S7.

(3) Effects

In the X-ray fluorescence analyzer 100 according to this embodiment, a part of the X-rays emitted by the X-ray source 30 is blocked by the collimator 40, and the other part of the X-rays passes through the sector-shaped opening 41 of the collimator 40. The vertex of the sector shape of the opening 41 is positioned on the axis of rotation R. Therefore, the X-rays passing through the opening 41 of the collimator 40 to be emitted to the respective portions of the sample S while the support unit 20 and the collimator 40 are relatively rotated by one revolution become spatially uniform. This makes it possible to spatially and uniformly attenuate the X-rays emitted to the sample S.

Further, in this embodiment, it is configured such that the collimator 40 is fixed and the support unit 20 rotates with respect to the collimator 40. This makes it possible to relatively rotate the support unit 20 and the collimator 40 about the axis of rotation R with a simple configuration.

(4) Modification of Collimator
(a) First Modification

Figure 5:
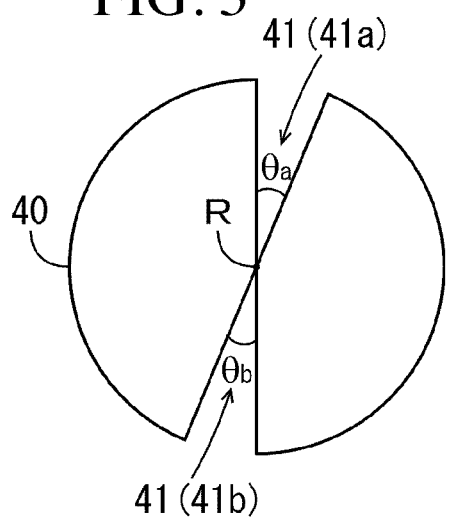
FIG. 5 is a plan view showing a first modification of a collimator.
Figure 6:
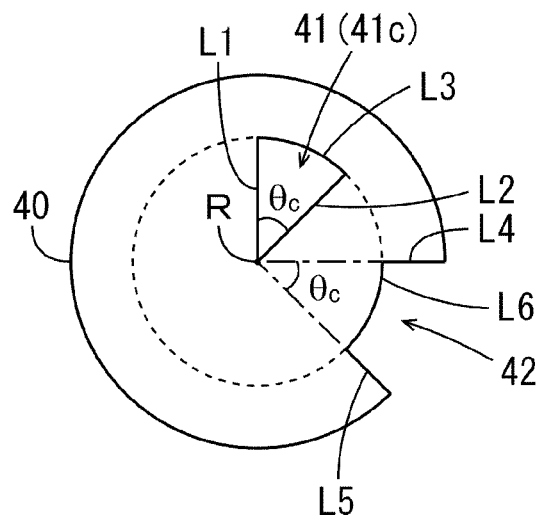
FIG. 6 is a plan view showing a first modification of a collimator.

FIG. 5 and FIG. 6 are plan views showing a first modification of the collimator 40. In the example of FIG. 5, two sector-shaped openings 41 are formed in the collimator 40. One of the openings 41 of FIG. 5 is referred to as an opening 41a, and the other opening 41 is referred to as an opening 41b. The central angle of the sector-shaped opening 41a and that of the opening 41b are θa and θb, respectively. In the example of FIG. 5, the sum of θa and θb is equal to the central angle θ of the opening 41 of FIG. 2. In this case, the collimator 40 of FIG. 5 is substantially equivalent to the collimator 40 of FIG. 2.

In the example of FIG. 6, a sector-shaped opening 41 and an annular sector-shaped opening 42 are formed in the collimator 40. The opening 41 of FIG. 6 is referred to as an opening 41c. The opening 41c has two straight edges L1 and L2 and an arcuate outer edge L3. The opening 42 has two straight edges L4 and L5 and an arcuate inner edge L6. The vertex of the sector-shaped opening 41c (the intersection of the two edges L1 and L2) overlaps with the axis of rotation R. The opening 42 is a cut-out portion, and the outer peripheral portion (arc) of the annular sector is exposed laterally from the side surface of the collimator 40.

The outer edge L3 of the opening 41c and the inner edge L6 of the opening 42 have the same length and are positioned on the circumference of a common circle indicated by a dotted line in FIG. 6. The angle formed by the edge L1 and the edge L2 is θc. Similarly, the angle formed by the edge L4 and the edge L5 is θc. In the example of FIG. 6, θc is equal to the central angle θ of the opening 41 of FIG. 2. In this case, the collimator 40 of FIG. 6 is substantially equivalent to the collimator 40 of FIG. 2. As described above, the opening 41 of FIG. 2 may be divided into a plurality of openings in the circumferential direction of the collimator 40 (see FIG. 5), or may be divided into a plurality of openings in the circumferential direction and in the radial direction of the collimator 40 (see FIG. 6).

(b) Second Modification

Figure 7:
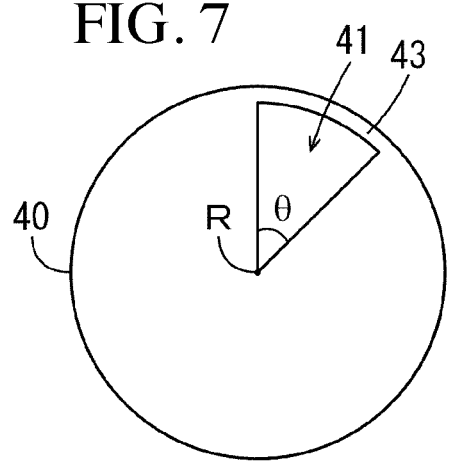
FIG. 7 is a plan view showing a second modification of a collimator.
Figure 8:
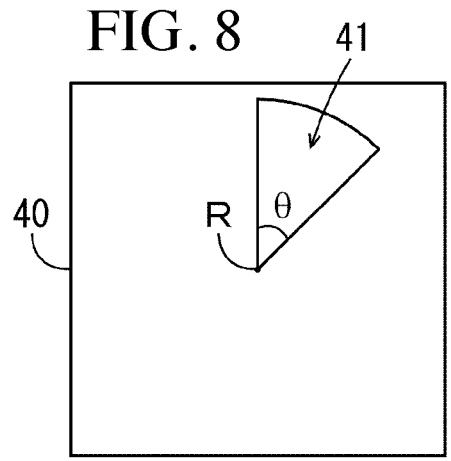
FIG. 8 is a plan view showing a second modification of a collimator.

In the above-described embodiments, the opening 41 is a cut-out portion, and the outer peripheral portion (arc) is exposed laterally from the side surface of the collimator 40, but the present invention is not limited thereto. FIG. 7 and FIG. 8 are plan views showing a second modification of the collimator 40. As shown in FIG. 7, it may be configured such that the outer peripheral portion 43 of the collimator 40 remains at the outer peripheral portion of the opening 41 and the outer peripheral portion of the opening 41 is not exposed to the side from the side surface of the collimator 40.

Further, as in the example shown in FIG. 8, the collimator 40 may have a rectangular shape. Alternatively, the collimator 40 may have other shapes, such as, e.g., an elliptical shape, an oval shape, or a polygonal shape. In the second modification, as in the example of FIG. 5, even in cases where a plurality of openings 41 is formed in the collimator 40, the collimator 40 can be integrally formed without the collimator 40 being divided into a plurality of parts.

(c) Third Modification

The collimator 40 may be configured such that the circumferential length (the length of the arc) of the sector-shaped opening 41, i.e., the central angle, may be changeable. In this case, the circumferential length of the opening 41 of the collimator 40 can be easily changed depending on the composition of the sample S. As a result, the X-rays can be uniformly attenuated to appropriate intensity depending on the composition of the sample S.

Figure 9:
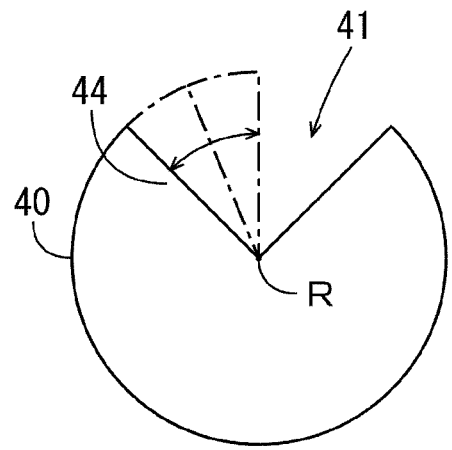
FIG. 9 is a plan view showing a third modification of a collimator.
Figure 10:
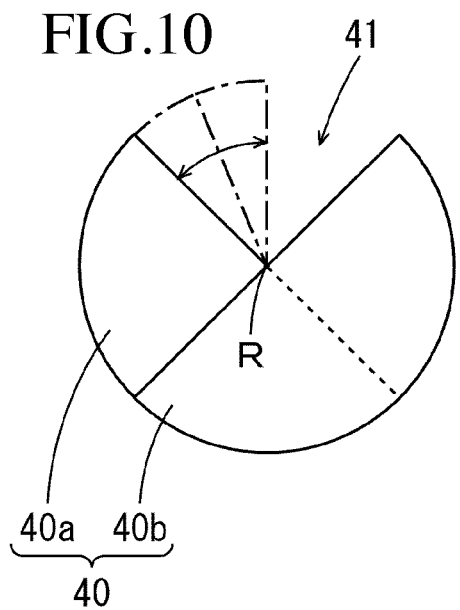
FIG. 10 is a plan view showing a third modification of a collimator.

FIG. 9 and FIG. 10 are plan views showing a third modification of the collimator 40. In the example FIG. 9, the end portion 44 of the collimator 40 (the portion adjacent to the opening 41) in the circumferential direction is formed drawable and retractable in the circumferential direction of the collimator 40. This allows the central angle of the sector-shaped opening 41 to be changed.

In the example of FIG. 10, the collimator 40 is composed of two semicircular shaped plate members 40a and 40b. The plate members 40a and 40b are stacked with the center of each semicircular overlapping with the axis of rotation R. Note that the center of the semicircle means the midpoint of the string. The sector-shaped opening 41 is formed between the half of the semicircular string of the plate member 40a and the half of the semicircular string of the plate member 40b. One of the plate members 40a and 40b is formed to be drawable and retractable in the circumferential direction with respect to the other. This allows the sector-shaped central angle of the opening 41 to be changed.

The plate members 40a and 40b may have, not a semicircular shape, but another sector shape, and may not have the same configuration. For example, in cases where the plate member 40a is formed in a semicircular shape and the plate member 40b is formed in a sector shape, the plate members 40a are 40b are stacked in a laminated manner in a state in which the center of the semicircle shaped plate member 40a and the vertex of the sector-shaped plate member 40b overlap with the axis of rotation R. Further, in cases where each of the plate members 40a and 40b is formed in a sector shape, the plate members 40a and 40b are laminated in a state in which the vertexes of the respective sectors overlap with the axis of rotation R.

(d) Fourth Modification

In the above-described embodiment, the opening 41 has a sector shape, but the present invention is not limited thereto. It is enough that the opening 41 has a shape in which the circumferential length increases proportionally at it advances from the vertex (the point at which the vertex overlaps with the axis of rotation R) outward and may not have a sector shape. Even in this case, the X-rays passing through the collimator 40 can be attenuated spatially and uniformly.

Figure 11:
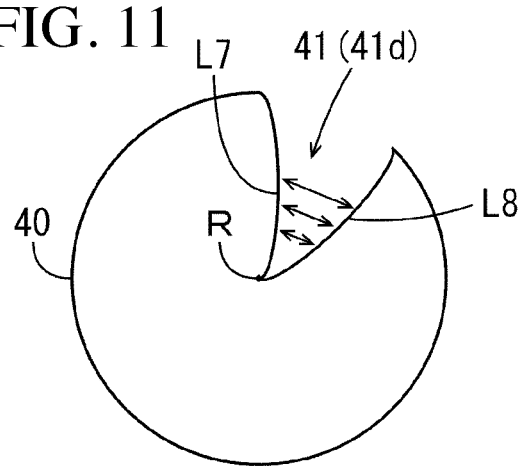
FIG. 11 is a plan view showing a fourth modification of a collimator.
Figure 12:
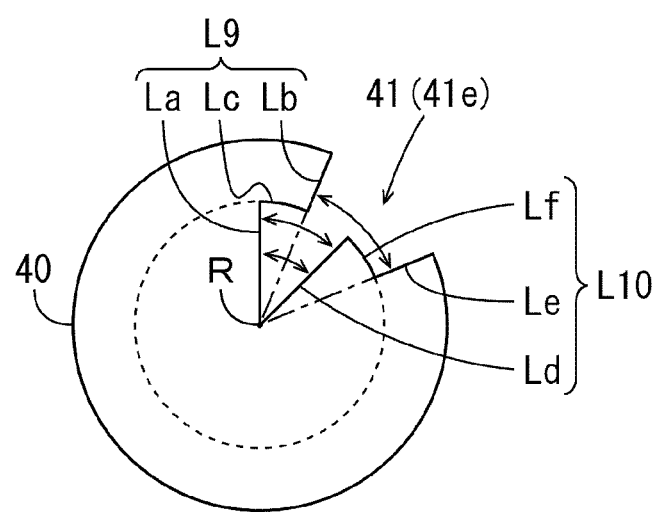
FIG. 12 is a plan view showing a fourth modification of a collimator.

FIG. 11 and FIG. 12 are plan views showing a fourth modification of the collimator 40. In the example of FIG. 11, The collimator 40 is formed with an opening 41 having a shape different from a sector shape. The opening 41 in FIG. 11 is referred to as an opening 41d. The opening 41d has two edges L7 and L8 extending outwardly from the position (vertex) that overlaps with the axis of rotation R while curving. When the edge L7 is virtually rotated about the axis of rotation R by a predetermined angle, the edge L7 overlaps with the edge L8. In this case, the circumference length of the opening 41d increases proportionally as it advances outward from the vertex.

Similarly, in the example of FIG. 12, the collimator 40 is formed with an opening 41 having a shape different from a sector shape. The opening 41 in FIG. 12 is referred to as an opening 41e. The opening 41e has two edges L9 and L10 that extend outward while bending from the position (vertex) overlapping with the axis of rotation R. Specifically, the edge L9 is composed of straight edges La and Lb and an arcuate edge Lc. The edge L10 is composed of straight edges Ld and Le and an arcuate edge Lf.

The edge La extends linearly outward from the position overlapping with the axis of rotation R. The edge Lb extends linearly from the outside of the collimator 40 toward the position overlapping with the axis of rotation R. The edge Lc connects the outer end of the edge La and the inner end of the edge Lb. The edge Ld extends linearly outward from the position overlapping with the axis of rotation R. The edge Le extends linearly from the outside of the collimator 40 toward the position overlapping with the axis of rotation R. The edge Lf connects the outer end of the edge Ld and the inner end of the edge Le.

The lengths of the edges La, Lb, and Lc are equal to the lengths of the edges Ld, Le, and Lf, respectively. The edge Lc and the edge Lf are located on the circumference of a common circle indicated by a dotted line in FIG. 12. The angle formed by the edge La and the edge Ld is equal to the angle formed by the edge Lb and the edge Le. Therefore, when the edges La, Lb, and Lc are virtually rotated by a predetermined angle about the axis of rotation R, the edges La, Lb, and Lc overlaps with the edges Ld, Le, and Lf, respectively. In other words, when the edge L9 is virtually rotated about the axis of rotation R by a predetermined angle, the edge L9 overlaps with the edge L10. In this case, the circumferential length of the opening 41e increases proportionally as it advances outward from the vertex.

(e) Fifth Modification

Figure 13:
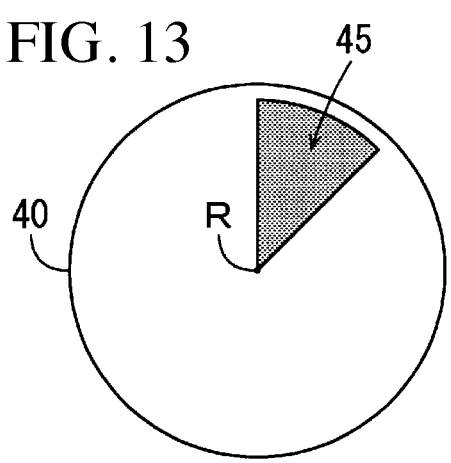
FIG. 13 is a plan view showing a fifth modification of a collimator.

In the above-described embodiments, the collimator 40 has an opening, but the present invention is not limited thereto. FIG. 13 is a plan view showing a fifth modification of the collimator 40. In the example of FIG. 13, in place of an opening, the collimator 40 has a transmission region 45 made of a material (e.g., glass) that allows X-rays to pass therethrough. In FIG. 13, the transmission region 45 is illustrated by a dot-pattern. The portion other than the transmission region 45 in the collimator 40 is a blocking region that blocks X-rays. Even in this case, it is possible to spatially and uniformly attenuate the X-rays passing through the collimator 40.

Note that the shape of the transmission region 45 may be the same as the shape of any opening described in the above-described embodiments or first to fourth modifications of the collimator 40. Further, the opening described in the first to fourth modifications and the transmission region described in the fifth modification may be combined to form a collimator 40.

The invention claimed is:

1. An X-ray fluorescence analyzer comprising:
    a support unit configured to support a sample to be analyzed;
    a collimator having a blocking region that blocks X-rays and a transmission region that allows X-rays to pass therethrough;
    an X-ray source configured to emit X-rays to the sample supported by the support unit through the transmission region of the collimator;
    a rotation driving device configured to relatively rotate the support unit and the collimator about an axis of rotation;
    a detector configured to detect fluorescent X-rays from the sample supported by the support unit; and
    an analysis execution unit configured to analyze a composition of the sample based on the fluorescent X-rays detected by the detector,
    wherein the transmission region has a vertex positioned on the axis of rotation,
    wherein a circumferential length of the transmission region increases proportionally as it advances outward from the vertex, and
    wherein the X-ray source emits the X-rays to each portion of the sample in a time-division manner in a state in which the collimator or the support unit is being rotated, such that the X-rays always pass across the transmission region and the blocking region of the collimator.

2. The X-ray fluorescence analyzer as recited in claim 1, wherein the transmission region has a sector shape.

3. The X-ray fluorescence analyzer as recited in claim 1, wherein the transmission region is an opening.

4. The X-ray fluorescence analyzer as recited in claim 1, wherein the collimator is fixed, and
    wherein the support unit is rotatable relative to the collimator.

5. The X-ray fluorescence analyzer as recited in claim 1, wherein the collimator is configured to be variable in a circumferential length of the transmission region.

6. The X-ray fluorescence analyzer as recited in claim 1, further comprising:
    an intensity control unit configured to control intensity of the X-rays emitted by the X-ray source.

7. The X-ray fluorescence analyzer as recited in claim 6, further comprising:
    a determination unit configured to determine whether or not a detection signal indicating a detection amount of the fluorescent X-rays detected by the detector is saturated,
    wherein the intensity control unit controls the X-ray source so that the intensity of X-rays emitted to an extent that the detection signal is not saturated increases based on a determination result by the determination unit.

8. The X-ray fluorescence analyzer as recited in claim 1, wherein a relative rotational rate between the collimator and the support unit is 720 degrees/sec.

9. The X-ray fluorescence analyzer as recited in claim 1, wherein the X-ray source is further configured to correct the intensity of the X-rays to be emitted to the sample based on a ratio of an area of the transmission region to an entire area of the collimator.

10. The X-ray fluorescence analyzer as recited in claim 1, wherein the collimator is configured to block a part of the X-rays emitted from the X-ray source and allow the other part of the X-rays to pass therethrough.

11. An X-ray fluorescence analysis method comprising the steps of:
    relatively rotating a support unit for supporting a sample to be analyzed and a collimator having a blocking region that blocks X-rays and a transmission region that allows X-rays to pass therethrough around an axis of rotation by a rotation driving device;
    emitting X-rays by an X-ray source to each portion of the sample supported by the support unit through the transmission region of the collimator in a time-division manner in a state in which the collimator or the support unit is being rotated;
    detecting fluorescent X-rays from the sample supported by the support unit by a detector; and
    analyzing a composition of the sample based on the fluorescent X-rays detected by the detector,
    wherein the transmission region has a vertex positioned on an axis of rotation,
    wherein a circumferential length of the transmission region increases proportionally as it advances outward from the vertex, and
    wherein the step of emitting X-rays by an X-ray source to each portion of the sample includes emitting the X-rays such that the X-rays always pass across the transmission region and the blocking region of the collimator.

12. The X-ray fluorescence analysis method as recited in claim 11,
wherein the step of rotating includes rotating the support unit relative to the collimator that is fixed.

* * * * *